United States Patent [19]

Matsuda et al.

[11] Patent Number: 5,411,881
[45] Date of Patent: May 2, 1995

[54] CHICKEN-SPECIFIC IMMUNOGLOBULIN G-PRODUCING HYBRIDOMA

[75] Inventors: Haruo Matsuda, Hiroshima; Shigeyuki Nishinaka; Takashi Suzuki, both of Tokyo, all of Japan

[73] Assignee: NKK Corporation, Tokyo, Japan

[21] Appl. No.: 838,775

[22] PCT Filed: Jul. 10, 1991

[86] PCT No.: PCT/JP91/00923
§ 371 Date: May 5, 1992
§ 102(e) Date: May 5, 1992

[87] PCT Pub. No.: WO92/01043
PCT Pub. Date: Jan. 23, 1992

[30] Foreign Application Priority Data

Jul. 10, 1990 [JP] Japan .................................. 2-182174

[51] Int. Cl.$^6$ ........................ C12N 5/00; C12N 15/00; C12N 5/16; C12N 15/06
[52] U.S. Cl. ............................ 435/240.27; 435/71.1; 435/172.2
[58] Field of Search ................. 435/71.1, 172.2, 240.27

[56] References Cited

PUBLICATIONS

Goding et al *Monoclonal Antibodies* 1986 pp. 59–97.
Ohashi et al *Cancer Research* Nov. 1986 46 pp. 5858–5863 Monoclonal Antibody to Chicken . . . .
Haruo Matsuda et al, Establishment of a Chicken X Chicken Hybridoma Secreting Specific Antibody, 1989, pp. 416–419.
International Archives of Allergy and Applied Immunology, vol. 89, No. 4, 1989, Basel, Switzerland pp. 416–419, S. Nishinaka et al., "Establishment of a chicken x chicken hybridoma secreting specific antibody".
Journal of Immunological Methods, vol. 139, No. 2, Jun. 3, 1991, Amsterdam, The Netherlands pp. 217–222, S. Nishinaka et al., "A new cell line for the production of chicken monoclonal antibody by hybridoma technology".

*Primary Examiner*—Herbert J. Lilling
*Attorney, Agent, or Firm*—Sughrue, Mion, Zinn, Macpeak & Seas

[57] ABSTRACT

A thymidine kinase-lacking hybrid cell having an Ig-producing ability in which chicken B lymphoblast with immunized chicken spleen cell, a method of obtaining the above hybrid cell which comprises mutating chicken B lymphoblast cell, isolating a thymidine kinase-lacking cell using a culture medium containing a thymidine analog, fusing it with immunized chicken spleen cell, mutating the hybrid cell, and isolating a thymidine kinase-lacking hybrid cell using a culture medium containing a thymidine analog, a hybrid cell having an IgG-producing ability in which a chicken spleen cell immunized with an antigen is further fused with the above hybrid cell, a method of producing a chicken IgG which comprises culturing the above hybrid cell having an IgG-producing ability in a culture medium. The antibody-producing cell of the invention can produce chicken IgG stably for a long period, and thereby it opens the way for the massproduction of chicken IgG.

7 Claims, 1 Drawing Sheet

CHICKEN-SPECIFIC IMMUNOGLOBULIN G-PRODUCING HYBRIDOMA

TECHNICAL FIELD

This invention relates to an established hybrid cell having an IgG-producing ability obtained from a chicken, its preparation method, a hybrid cell having an IgG-producing ability obtained by fusing the established hybrid cell with an immunized chicken spleen cell, and a method of producing an antibody utilizing this hybrid cell.

BACKGROUND ART

It is known that chicken-immunized globulin IgG has a very low cross-reactivity with IgG derived from a mammal (Hadge, D., et al, Mol. Immunol., 21, 699-707, 1984). Moreover, it is also known that the chicken IgG does not bind protein A (Guss, B. et al, EMBO J., 5, 1567-1575, 1986). Furthermore, the chicken antibodies have the advantages of not activating the complement system and not reacting with the rheumatoid factor in mammalian sera (Larsson, A., et al, I. Immunol. Methods, 108, 205-208, 1988). Thereupon, an assay for measuring circulating immune complexes using a chicken anti-human complement antibody has recently been established (Largson, A., et al, J. Immunol. Methods, 113, 93-99, 1988). These facts indicate that chicken antibody is extremely useful in mammalian immunology field. Therefore, it is considered that, if chicken monoclonal antibody can be supplied, the antibody is utilized as a useful means not only in the field of avian immunology but also in that of mammalian immunology.

The present inventors eagerly investigated in order to establish a parental cell line for the preparation of chicken monoclonal antibody, and examined to establish the cell line from chicken B cells, similar to mouse myeloma cell. As a result, we obtained a cell which can grow stably among thioguanine-resistant cells. However, all of the thioguanine-resistant cells have HAT (hypoxanthine-aminopterin-thymidine) resistance. Thereupon, we further investigated, and as a result, we established a thymidine kinase-lacking cell line with HAT sensitivity which can stably multiply. Thus, we found that, when the established cell was fused with an immunized chicken spleen cell, a chicken monoclonal antibody could be accumulated in a culture medium by culturing the fused cell (specification of Japanese patent application No. 1-5781, Int. Arch. Allergy Appl. Immunol., 89, 416-419 (1989)).

As mentioned previously, it is considered that if chicken monoclonal antibody can be supplied, the antibody is utilized as a useful means not only in the filed of arian immunology but also in that of mammalian immunology. Such a technique is limited to that developed by the inventors which is the first one. However, since the antibody-producing cell previously developed was inferior in stability, there were problems that not only its subculture for a long period was difficult, but also its antibody-producing ability disappeared during a long culture. Furthermore, since the produced antibody was IgM, the development of IgG-producing cell was desired in view of utilization.

The present invention has been made is order to resolve the above problems, and an object of the invention is to obtain a hybrid cell which can subculture for a long period with the antibody-producing ability, and of which antibody produced is in IgG class.

DISCLOSURE OF INVENTION

The above object has been achieved by an established thymidine kinase-lacking hybrid cell having an IgG-producing ability which is a chicken B lymphoblast fused with an immunized chicken spleen cell obtained by mutating a chicken B lymphoblast cell line, isolating a thymidine kinase-lacking cell using a culture medium containing a thymidine analog, fusing an immunized chicken spleen cell, mutating the hybrid cell and isolating an established thymidine kinase-lacking hybrid cell using a culture medium containing a thymidine analog, and by a hybrid cell having an IgG-producing ability obtained from the above one by fusing a chicken spleen cell immunized with an antigen. Chicken IgG can be produced stably for a long period by culturing the hybrid cell having a IgG-producing ability.

BEST MODE FOR CARRYING OUT THE INVENTION

Figure 1:
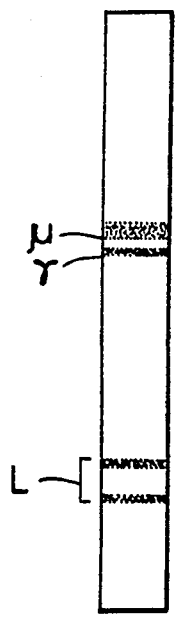
FIG. 1 shows a developed color pattern obtained during examining a culture supernatant of an antibody-producing cell of the invention by the western blotting method after conducting electrophoretic migration.

The established thymidine kinase-lacking hybrid cell is obtained from chicken B lymphoblast. The kind of chicken is not limited, and for example, white leghorn, white rock and the like can be utilized.

Avian B lymphoblast cell line is obtained from chicken or B lymphocyte by suffering from cancer by an avian retrovirus.

The B lymphoblast cell line having self proliferation potency thus obtained is mutated, and thymidine kinase-lacking cells are selected. The mutation may be conducted by a physical means, such as UV irradiation, or by utilizing an agent, such as ethyl methanesulfonic acid, nitrosoguanidine or ICR-191. The isolation of the thymidine kinase-lacking cell from the mutant cells may be conducted, for example, by culturing in a culture medium containing a thymidine analog, such as trifluorothymidine or bromodeoxyuridine, and cloning. The culture medium may be a conventional medium for cell culture, for example, RPMI 1640 medium, Dalbecco's modified MEM medium or the like to which 5-15% of fetal bovine serum (FBS) or the like is added. The culture conditions may also be similar to conventional cell culture, and for example, may culture at about 37°-41° C. in an atmosphere of air to which about 5-10% of $CO_2$ is added.

The established thymidine kinase-lacking cell thus obtained has self proliferation potency, but it dies by culturing in a HAT medium. Besides, when it is measured by the indirect fluorescent antibody method, no cell synthesizes the chicken Ig. This cell is designated as HU3 R cell.

The HU3 R cell is fused with an immunized chicken spleen cell. The spleen cell may be prepared by injecting several times an antigen, such as inactivated Newcastle disease virus, together with an adjuvant into chicken, and excising it after breeding. The fusion is conducted by a known cell fusion technique, such as polyethylene glycol, electric fusion or HVJ virus.

The hybrid cell obtained is further mutated, and thymidine kinase-lacking cell line is selected. It is preferable that these treatments are conducted after the subculture of the hybrid cell is continued until the growth is stable. The mutation treatment and the selection of thymidine kinase-lacking cells may be conducted similar to the aforementioned method. Besides, if necessary, mutation means, conditions may be changed. The production of Ig can be detected by detecting γ chain, μ chain and L chain which are a part of Ig, and the detection of these chains may be conducted according to a known method. For example, the indirect fluorescent antibody method using an anti-chicken Ig anti γ chain antibody and a fluorescein-labeled second antibody, flow cytometry, etc. can be utilized. The production of Ig can be confirmed by the confirmation of one or γ chain, μ chain or L chain.

The established hybrid cell having Ig-producing ability thus obtained is further fused with an immunized chicken spleen cell. The immunization and the fusion may be similar to the aforementioned method. Since the antigen used for the appearance of immune is considered to impart IgG-producing ability to the cell after fused with the immunized chicken spleen cell, the antigen is selected according to the desired IgG.

The IgG may be produced by culturing the hybrid cell similar to the aforementioned method, and the IgG can be produced and accumulated in the culture supernatant by culturing for about 1–30 days. The separation may be conducted by utilizing a known means, and affinity chromatography, gel filtration, ion exchange chromatography, ethanol fractionation, rivanol fractionation, PEG fractionation, etc. are applicable.

EXAMPLES

Example 1

A virus-nonproducing B lymphoblast cell line RECC-HU3 (hereinafter abbreviated as HU3 cell line), which has been established from chicken by an in vitro transformation method using avian reticuloendotheliosis virus, was fused with chicken spleen cell to obtain a L chain-producing type hybridoma, and the hybridoma subcultured was used as the cell line to be tested. The hybridoma was obtained from HU3 cell line by treating with ethyl methanesulfonic acid (EMS), isolating HU3 R27 cell line (FERM P-10484, BP-3473) which is a thymidine kinase (TK)-lacking cell line, and fusing this with a chicken spleen cell immunized with inactivated Newcastle disease virus (NDV), and the production of L chain has already not been observed by the cultivation for a long period.

$5 \times 10^6$ cells to be tested was suspended in 25 ml of RPMI 1640 medium containing 5% FBS, and put into a 100 mm culture dish. The cells were cultured at 38.5° C. for 6 hours in a 5% CO$_2$ incubator. EMS was added in a concentration of 600 μg/ml, and further cultured for 24 hours. After 24 hours, the cells were washed with RPMI 1640 medium, and then suspended in 25 ml of RPMI 1640 medium containing 10% FBS. After culturing for 3 days, trifluorothymidine (TFT) was added thereto in a concentration of 1 μg/ml, and further continued the cultivation. The multiplied cells were gradually increased in the same medium. When the multiplication became stable, the TFT concentration of the medium was gradually elevated, and stably multiplied cells at 10 μg/ml were used as TK-lacking cells.

The TK-lacking cells were cloned by the soft agar method, and the following 4 cell clones were obtained. The medium used was an IMDM medium containing 0.35% Norble agar, 10% FBS and 40% HU3 R culture supernatant. Properties of 4 clones obtained, R27H1 (FERM P-11543, FERM BP-3475), R27H2 (FERM P-11544, FERM BP-3476), R27H3 (FERM P-11545, FERM BP-3477) and R27H4 (FERM P-11546, FERM BP-3478) and the parental cell line therof of HU3 R27 (FERM P-10484, FERM BP-3473) are shown in Table 1.

TABLE 1

|  | Ig Secretion | Cell Surface Ig | | | Doubling Time (hr) |
| --- | --- | --- | --- | --- | --- |
|  |  | L | γ | μ |  |
| HU3 R27 | — | 0 | 0 | 0 | 18.04 |
| R27H1 | μ | 45.3 | 29.1 | 51.7 | 17.29 |
| R27H2 | IgM | 85.9 | 18.9 | 88.8 | 19.93 |
| R27H3 | L | 27.1 | 10.8 | 20.3 | 16.97 |
| R27H4 | IgM | 71.1 | 7.3 | 62.1 | 13.80 |

In Table 1, the Ig secretion was examined by the western blotting method. The cell surface Ig was determined by the flow cytometry. The doubling time was determined by the measurement of the number of cells. As shown in Table 1, the secretion of IgM, μ chain or L-chain were observed in 4 cell lines. The production of L chain, μ chain and γ chain was observed on the cell surfaces.

Example 2

Each of the above clones were fused with a spleen cell immunized by injecting Keyhole Limpet haemocyanin (KLH).

The cell fusion was conducted as follows: First, each clonal cell was recovered in a 50 ml centrifuge tube made of polypropylene, and washed three times with RPMI 1640 medium not containing serum. The clonal cell was mixed with the chicken spleen cell immunized with KLH at a ratio of 1:5, and centrifuged at 267 G for 5 minutes. After centrifuging, the supernatant was completely removed by suction. The agglutination of cells was loosened by tapping the bottom of the centrifuge tube lightly, and warmed in a constant temperature bath at 38° C. To the cells, 1 ml of PEG solution which was previously warmed at 38° C. was added for 1 minute. At this time, the solution was occasionally stirred by the tip of the pipette with shaking the centrifuge tube forward and backward and right and left. After finishing the addition of the PEG solution, it was allowed to stand for 1 minute. Subsequently, 10 ml of RPMI 1640 medium not containing serum which was warmed at 38° C. was gradually added for about 5 minutes, and the reaction was terminated. About 30 ml of the same medium was further added, and centrifuged at 267 G for 5 minutes. After centrifuging, the supernatant was gently removed by suction. IMDM medium containing 10% FBS was added, and the cell sediment was loosened. Each 0.1 ml of the above cell suspension was put into a 96 well plate for tissue culture, and cultured at 38.5° in a 5% CO$_2$ incubator.

The selection of hybrid cells were conducted as follows: First, after 24 hours from the fusion, 100 μl of HAT (twice the concentration) medium was added to each well of the 96 well plate for tissue culture. After 2 days from the fusion, the medium was exchanged for HAT medium in the normal concentration at an interval of 2–3 days, and cultured for 10–14 days in HAT medium. After the cultivation in the HAT medium for 10–14 days, the medium was changed for HT medium, and cultured for 1 week. Thereafter, IMDM medium was used, and the amount was increased according to the increase of cells.

Thus, the immunized spleen cell was fused with each clone of R27H1 (FERM P-11543, FERM BP-3475), R27H2 (FERM P-11544, FERM BP-3476), R27H3 (FERM P-11545, FERM BP-3477) and R27H4 (FERM P-11546, FERM BP-3478). Although the hybridoma could not be obtained at the beginning, the hybridoma was gradually obtained according to the continuation of the subculture of each clone for a long period.

A hybridoma of which the parental cell line was R27H4 was cultured in IMDM medium containing 10% FBS. The culture supernatant was subjected to polyacrylamide gel electrophoresis (SDS-PAGE), and the western blotting method was conducted. That is, after the electrophoretic migration, the migrants were transferred to a nitrocellulose paper, and allowed to react with anti-chiken $\mu$, $\gamma$ and L antibodies labeled with horse-radish peroxidase. Then, color was developed by dimethylaminobenzene (DAB) to obtain the pattern shown in FIG. 1. As shown in the figure $\gamma$ chain which is H chain portion of IgG in addition to $\mu$ chain which is H chain portion of IgM appear in the culture supernatant of a hybridoma derived from R27H4, and L chain also appears to indicate the production of both of IgG and IgM.

Figure 2:
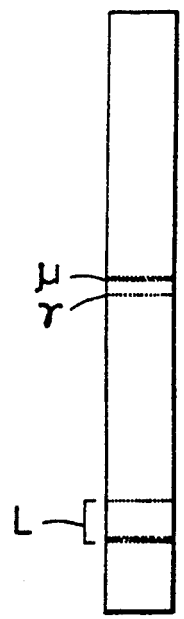
FIG. 2 shows a developed color pattern obtained during examining a culture supernatant of an antibody-producing cell of the invention by the western blotting method after conducting electrophoretic migration.
Figure 3:
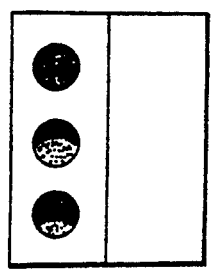
FIG. 3 shows a color developed state obtained during examining the above culture supernatant by the dot blotting method.

Another color developed pattern is shown in FIG. 2 which was obtained from the culture supernatant of a hybridoma (HU/Ch22-4, FERM-BP-3474) of which the parental cell line was R27H1 by conducting SDS-PAGE followed by the western blotting method as mentioned above. As shown in the figure, $\gamma$ was detected in addition to $\mu$ chain, and L chain was also detected. Thus, the production of both of IgG and IgM was confirmed. The production of Ig was observed in most of the hybrid cells obtained from R27H series as the parental cell line. Since the ratio of B lymphocyte in the spleen of chicken is about 30%, it cannot be considered that all of the hybrid cells obtained were produced by fusing with B lymphocyte, but it is considered that these Ig were produced in the parental cell and secreted by the fusion. Therefore, it is considered that the IgM in the above Ig is derived from the parental cell and the IgG is derived from the spleen cell, and it is considered that the IgG has a specificity to the antigen. Then, this matter was examined by the ELISA method and the dot blotting method. In the ELISA method, 50 $\mu$l of 2 $\mu$g/ml KLH was immobilized onto a microplate, and 50 $\mu$l of the culture supernatant was added. An anti-chicken immunoglobulin antibody bound to HRP was further added. After mixing, substrates for HRP ($H_2O_2$ and DAB) were added to develop color, and examined. In the dot blotting method, KLH was spotted onto nitrocellulose paper and allowed to react with the culture supernatant. Subsequently, anti-chicken $\gamma$, $\mu$ and L antibodies labeled with HRP were allowed to react. Thereafter, substrates for HRP ($H_2O_2$ and DAB) were added to develop color. As a result, both measuring methods indicated that, among Ig produced, mainly IgG has a strong reactivity to KLH. The developed color according to the dot blotting method is shown in FIG. 3. The spots in the figure shows the reactivities of $\mu$ chain, $\gamma$ chain, L chain from the top, and the left side of the figure shows the reactivity of H chain of IgG and the right side shows the reactivity of H chain of IgM, respectively.

As to the productivity of Ig, in the case that HU3 R27 was used as the parental cell, the Ig-producing duration of the hybridomas obtained was short, and Ig-producing hybridoma could not obtained. Contrarily, in the case of the above hybridomas, the production of the specific antibody was observed even after the cultivation for about 3 months. The isolation of a clone of the specific antibody-producing hybridoma was succeeded by cloning according to the soft agar method.

The producing ability of IgG was measured by subculturing the hybridoma (HU/Ch22-4, FERM P-11542, FERM BP-3474) obtained from R27H1 cell as the parental cell and the cell obtained by the above cloning in IMDM medium containing 10% FBS, and after fusion, measuring the culture supernatant recovered with time by the aforementioned ELISA method. The results are shown below.

| After Fusion | 16 days | 26 days | 42 days | 49 days |
|---|---|---|---|---|
| O.D. 490 nm | 0.875 | 1.187 | 1.538 | 1.495 |

The other 9 clones were also measured by the ELISA method similarly, and the variation of absorbance is shown in Table 2.

TABLE 2

| Clone No./After Fusion | O.D. 490 nm | | |
|---|---|---|---|
| | 33 days | 38 days | 41 days |
| 1 | 1.593 | 1.494 | 1.682 |
| 2 | 1.613 | 1.444 | 1.546 |
| 3 | 1.533 | 1.056 | 1.566 |
| 4 | 0.709 | 0.912 | 1.109 |
| 5 | 0.905 | 1.545 | 0.863 |
| 6 | 1.792 | 1.653 | 1.619 |
| 7 | 1.444 | | 1.410 |
| 8 | 1.521 | | 1.526 |
| 9 | 1.690 | | 1.661 |

Example 3

HD antibody is a heterophil antibody reported by Hanganutziu and Deicher, and was considered that a causative antibody for serum sickness, because this antibody increased in the serum of a patient injected with an animal serum. However, recently, it has become apparent that the antibody is detected in various diseases such as cancer regardless of the injection of animal serum, and HD antigen can be expected as a marker for these diseases. It was ascertained that the antigen is a glycolipid and glycoprotein having N-glycolylneuraminic acid lNeuGc) at the nonreducing end sugar chain, and the antigen has an immunogenicity to human and chicken. Several kinds of the HD antigen are known. Some examples thereof are shown below.

HD3: NeuGc($\alpha$2–3)Gal($\beta$1–4)Glc-ceramide

HD5: NeuGc($\alpha$2–3)Gal($\beta$1–4)GlcNAc($\beta$1–3)Gal(-$\beta$1–4) Glc-ceramide HD7: NeuGc($\alpha$2–3)Gal($\beta$1–4)GlcNAc($\beta$1–3)Gal(-$\beta$1–4) GlcNAc($\beta$1–3)Gal($\beta$1–4)Glc-ceramide 4-O-acetyl-HD3: 4-O-acetyl-NeuGc($\alpha$2–3)Gal(-$\beta$1–4)Glc-ceramide In order to prepare a monoclonal antibody to HD antigen, the spleen cell immunized by injecting the above HD3 antigen into chicken was fused with R27H4 cell line (FERM P-11546, FERM BP-3478). The cell fusion and the selection of hybrid cells were conducted similar to Example 2. As the culture medium after cell fusion, RPMI 1640 and IMDM medium were used. As a result, hybridomas obtained (hybridoma producing specific antibody to HD antigen) were 443 cells in the total as shown in Table 3. The specificity of the culture supernatant to HD3 was examined by the ELISA method, and the specificity was confirmed in 74 cells. In the ELISA method, 50 μl of 1 μg/ml HD3 was immobilized onto a microplate, and the culture supernatant was allowed to react. HRP-labeled anti-chicken immunoglobulin antibody was further added to react, and thereafter, HRP substrate (OPD) was added to react, and examined.

TABLE 3

| Cell Line | Culture Medium | Hyb./total | Spec./Hyb. |
| --- | --- | --- | --- |
| | RPMI 1640 | 68/864 | 12/68 |
| R27H4 | IMDM | 273/576 | 41/273 |
| | RPIM 1640 | 102/912 | 19/102 |

The hybridomas in which the specificity was observed were cultured for a long period, and after cloning, hybridomas particularly stably producing immunoglobulin to HD3 were examined as to the type of the immunoglobulin, the titer of the obtained culture supernatant and the specificity. The type of the immunoglobulin produced from the hybridoma was determined by the western blotting method in Example 2, after conducting SDS-PAGE of the culture supernatant of the hybridoma. As a result, it was ascertained that the type of the goblins produced by both hybridomas examined was IgG type as shown in Table 4. The measurement of the titer of the hybridoma culture supernatant was conducted by the ELISA method as above mentioned. That is, an antigen was immobilized onto a plate for ELISA, and the hybridoma culture supernatants which were diluted stepwise were allowed to react. HRP-labeled anti-chicken immunoglobulin antibody was allowed to react, and then, OPD was added to react. As a result, the titers were 1:80 and 1:360, respectively, as shown in Table 4.

TABLE 4

| Hybridoma | ELISA titer | Ig type |
| --- | --- | --- |
| HU/Ch2 (FERM BP 3472) | 1:80 | IgG |
| HU/Ch6 | 1:360 | IgG |

The antigenic specificity of the immunoglobulin was examined by the TLC immunostaining method. In the TLC immunostaining method, HD3.HD5.HD7 and 4-oAc-HD3 were developed on a thin layer gel for TLC by chloroform.methanol. potassium chloride solvent, and dried. The hybridoma culture supernatant was allowed to react, and HRP-labeled anti-chicken immunoglobulin was allowed to react. Then, color was developed by DAB. As a result, it was ascertained that the culture supernatants of the examined 2 hybridomas react with HD3.HD5.HD7 and 4-oAc-HD3 and HD3 and HD7, as shown in Table 5.

TABLE 5

| Specificity | HD3 | HD5 | HD7 | 4-o-Ac-HD3 |
| --- | --- | --- | --- | --- |
| HU/Ch2 | + | + | + | + |
| HU/Ch6 | + | − | + | − |

INDUSTRIAL APPLICABILITY

The antibody-producing cell of the invention can produce chicken-IgG stably for a long period, and thereby, it opens the way for the massproduction of chicken IgG. Since IgG is the largest in quantity and the greatest in universality, the meaning capable of massproducing chicken IgG of which the cross reactivity with human IgG is low. At present, the production of monoclonal antibodies is conducted using a mammal, such as mouse or rat. However, in the case that the antigen is derived from a mammal, such as human, the mouse or rat was occasionally not sensitized, even though it was stimulated by a human antigen. As a result, the monoclonal antibody was not produced. The present invention provides a way for producing the monoclonal antibody even in such a system. Accordingly, the present invention has an effect that the utilization range of antibodies further extends in assays of biological trace components as medicines and clinical assay reagents.

We claim:

1. The hybrid cell HU/Ch 22-4 (FERM BP-3474).

2. A method of producing a hybrid cell with IgG-producing capability, comprising
   mutating a chick B lymphoblast cell,
   isolating a thymidine kinase-deficient cell by culturing the resulting mutated cell in a medium containing a thymidine analog, fusing the resulting isolated thymidine kinase-deficient cell comprising chicken B lymphoblast cell HU3 R27 (FERM P-10484, BP-3473) with an immunized first chicken spleen cell to produce a first fusion product,
   mutating the first fusion product,
   isolating a thymidine kinase-deficient hybrid cell by culturing the resulting mutated first fusion product in a medium containing a thymidine analog, and
   fusing the resulting isolated thymidine kinase-deficient hybrid cell with an immunized second chicken spleen cell to produce said hybrid cell with IgG-producing capability.

3. The method of claim 2, wherein the thymidine kinase-deficient hybrid cell is a member selected from the group consisting of R27H1 cell (FERM P-11543, FERM BP-3475), R27H2 cell (FERM P-11544, FERM BP-3476), R27H 3 cell (FEPM P-11545, FERM BP-3477) and R27H4 cell (FERM P-11546, FERM BP-3478).

4. The method of claim 2, wherein said hybrid cell with IgG-producing capability is HU/Ch 22-4 (FERM BP-3474).

5. A method of producing chicken IgG, comprising culturing a hybrid cell with IgG-producing capability in a culture medium, and recovering said chicken IgG,
   wherein said hybrid cell with IgG-producing capability comprises a fusion product of an immunized second chicken spleen cell and a thyroidinc kinase-deficient hybrid cell,
   wherein said thymidine kinase-deficient hybrid cell comprises a fusion product of a chicken B lymphoblast cell HU3 R27 (FERM P-10484, BP-3473) and an immunized first chicken spleen cell, and
   wherein said hybrid cell with IgG-producing capability.

6. The method of claim 5, wherein the thymidine kinase-deficient hybrid cell is a member selected from the group consisting of R27H1 cell (FERM P-11543, FERM BP-3475), R27H 2 cell (FERM P-11544, FERM BP-3476), R27H3 cell (FERM P-11545, FERM BP-3477) and R27H4 cell (FERM P-11546, FERM BP-3474).

7. The method of claim 5, wherein said hybrid cell with IgG-producing capability is HU/Ch 22-4 (FERM BP-3474).

* * * * *